US006495605B2

(12) United States Patent
McCullough et al.

(10) Patent No.: US 6,495,605 B2
(45) Date of Patent: *Dec. 17, 2002

(54) METHODS AND COMPOSITIONS FOR AIDING IN SMOKING CESSATION AND FOR TREATING PAIN AND OTHER DISORDERS USING OPTICALLY PURE (+)-BUPROPION

(75) Inventors: John R. McCullough, Hudson, MA (US); Paul D. Rubin, Sudbury, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/803,956

(22) Filed: Mar. 13, 2001

(65) Prior Publication Data

US 2001/0011103 A1 Aug. 2, 2001

Related U.S. Application Data

(62) Division of application No. 09/238,984, filed on Jan. 28, 1999.
(60) Provisional application No. 60/072,933, filed on Jan. 29, 1998.

(51) Int. Cl.[7] .................. A01N 33/02; A61K 31/135
(52) U.S. Cl. ........................................ 514/646
(58) Field of Search ...................... 424/423; 514/646

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,622,675 A | 11/1971 | Koppe et al. | |
| 3,630,200 A | 12/1971 | Higuchi | |
| 3,819,706 A | 6/1974 | Mehta | |
| 3,845,770 A | 11/1974 | Theeuwes et al. | |
| 3,885,046 A | 5/1975 | Mehta | |
| 3,916,899 A | 11/1975 | Theeuwes et al. | |
| 3,960,927 A | 6/1976 | Metcalf et al. | |
| 4,008,719 A | 2/1977 | Theeuwes et al. | |
| 4,347,176 A | 8/1982 | Mehta | |
| 4,347,177 A | 8/1982 | Phillips | |
| 4,347,178 A | 8/1982 | Findlay et al. | |
| 4,347,257 A | 8/1982 | Stern | |
| 4,347,382 A | 8/1982 | Scharver | |
| 4,355,179 A | 10/1982 | Findlay et al. | |
| 4,356,165 A | 10/1982 | Findlay et al. | |
| 4,393,078 A | 7/1983 | Peck | |
| 4,425,363 A | 1/1984 | Stern | |
| 4,435,449 A | 3/1984 | Stern | |
| 4,438,138 A | 3/1984 | Stern | |
| 4,507,323 A | 3/1985 | Stern | |
| 4,571,395 A | 2/1986 | Peck | |
| 4,656,026 A | 4/1987 | Coffman et al. | |
| 4,687,660 A | 8/1987 | Baker et al. | |
| 4,769,027 A | 9/1988 | Baker et al. | |
| 4,798,826 A | 1/1989 | Peck | |
| 4,835,147 A | 5/1989 | Roberts | |
| 4,868,344 A | 9/1989 | Brown | |
| 4,895,845 A | 1/1990 | Seed | |
| 4,935,429 A | 6/1990 | Dackis et al. | |
| 4,935,439 A | 6/1990 | Kashman et al. | |
| RE33,994 E | 7/1992 | Baker et al. | |
| 5,217,987 A | 6/1993 | Berger | |
| 5,358,970 A | 10/1994 | Ruff et al. | |
| 5,427,798 A | 6/1995 | Ludwig et al. | |
| 5,447,948 A | 9/1995 | Seibyl et al. | |
| 5,512,593 A | 4/1996 | Dante | |
| 5,541,231 A | 7/1996 | Ruff et al. | |
| 5,731,000 A | 3/1998 | Ruff et al. | |
| 5,753,712 A | 5/1998 | Pinsker | |
| 5,763,493 A | 6/1998 | Ruff et al. | |
| 6,110,973 A | * 8/2000 | Young | 514/649 |
| 6,274,579 B1 | * 8/2001 | Morgan et al. | 514/238.8 |

FOREIGN PATENT DOCUMENTS

| | | |
|---|---|---|
| CA | 977777 | 11/1975 |
| CA | 977778 | 11/1975 |
| EP | 0 118 036 | 9/1984 |
| EP | 0 171 227 | 2/1986 |
| EP | 0 467 488 | 1/1992 |
| JP | 63-91352 | 4/1988 |
| WO | WO 91/11184 | 8/1991 |
| WO | WO 92/19226 | 11/1992 |
| WO | WO 93/21917 | 11/1993 |
| WO | WO 94/04138 | 3/1994 |
| WO | WO 94/20100 | 9/1994 |
| WO | WO 95/03791 | 2/1995 |
| WO | WO 95/22324 | 8/1995 |
| WO | WO 96/39133 | 12/1996 |
| WO | WO 97/29735 | 8/1997 |
| WO | WO 98/50044 | 11/1998 |
| WO | WO 99/37305 | 7/1999 |

OTHER PUBLICATIONS

Ascher, J.A. et al., 1995, "Bupropion: a review of its mechanism of antidepressant activity", J. Clin. Psych. 56:395–401.

Bannon et al., 1998, "Broad–spectrum, non–opoid analgesic activity by selective modulation of neuronal nicotinic acetylcholine receptors", Science 279:77–81.

(List continued on next page.)

Primary Examiner—Alton Pryor
(74) Attorney, Agent, or Firm—Pennie & Edmonds LLP

(57) ABSTRACT

Methods and compositions are disclosed utilizing the optically pure (+)-isomer of bupropion to assist in smoking cessation, for treating smoking and nicotine addiction, and for treating pain, including, but not limited to, chronic pain, neuropathetic pain and reflex sympathetic dystrophy, and other disorders such as narcolepsy, chronic fatigue syndrome, fibromyalgia, seasonal affective disorder and premenstrual syndrome, while avoiding adverse affects associated with racemic bupropion.

62 Claims, No Drawings

OTHER PUBLICATIONS

Bischoff et al., 1984, "Affinity changes of rat striatal dopamine receptor in vivo after acute bupropion treatment", Eur. J. Pharmaco. 104:173–176.
Blondel–Hill et al., 1993, "Treatment of the chronic fatigue syndrome", Drugs 46(4):639–651.
Borowski, T.B. et al., 1993, "Amphetamine and antidepressant drug effects on GABA– and NMDA–related seizures", Brain Res. Bull. 30:607–610.
Calabrese, J.R. et al., 1991, "Treatment of depression", Primary Care 18(2):421–433.
Castaldi, G. et al., 1987, Tartaric acid, an efficient chiral auxiliary: new asymmetric synthesis of 2–alkyl–2–arylacetic acids, J. Org. Chem. 52:3018–3027.
Castello, R.A. et al., "Discoloration of Tablets Containing Amines and Lactose", University of Michigan, Ann Arbor, College of Pharmacy, pp. 106–108 (1961).
Charney, D.S. et al., 1983, "Monoamine receptor sensitivity and depression: clinical studies of antidepressant effects on serotonin and noradrenergic function", Psychopharmacol. Bull. 19(3):490.
Clay et al., 1988, "Clinical and neuropsychological effects of the novel antidepressant bupropion", Psycopharma. Bull. 24(1):143–148.
Cooke C.E., 1997, "Therapeutic advances in the treatment of cigarette addiction", J. Pharmacy Practice 10(5):329–337.
Conners, K.C. et al., 1996, "Bupropion hydrochloride in attention deficit disorder with hyperactivity", J. Am. Acad. Child Adolesc. Psychiatr. 34(10):1314–1321.
Cooper, B.R. et al., 1994, "Evidence that the acute behavioral and electrophysiological effects of bupropion (Wellbutrin®) are mediated by a noradrenergic mechanism", Neuropsychopharmacology 11(2):133–141.
Cooper, T.B. et al., "Analytical psychopharmacology", Analytical Psychopharmacology: NY State Psychiatric Institute pp. 1–3.
Coutts, R.T. & Baker, G.B., 1989, "Implications of chirality and geometric isomerisms in some psychoactive drugsand their metabolites", Chirality 1:99–120.
Crenshaw et al., 1987, "Pharmacological modification of psychosexual dysfunction", J. Sex. Marital Ther. 13(4):239–252.
Cusack, B. et al., 1994, "Binding of antidepressants to human brain receptors: focus on newer generation compounds", Psychopharmacol. 114:559–565.
Davidson et al., 1994, "Bupropion in chronic low back pain", J. Clin. Psychiatry 55(8):362.
Dilsaver, S.C. et al., 1992, "The efficacy of bupropion in winter depression: results of an open trial", J. Clin. Psychiatry 53(7):252–255.
Eliel, E.L., 1962, *Stereochemistry of Carbon Compounds*, McGraw–Hill, NY.
Ferris & Beaman, 1983, "Bupropion: a new antidepressant drug, the mechanism of action of which is not associated with down–regulation of postsynaptic β–adrenergic, serotonergic (5–HT$_2$), α$_2$–adrenergic, imipramine and dopaminergic receptors in brain", Neuropharmacol. 22(1):1257–1267.
Ferris, R.M. et al., 1983, "Studies of bupropion's mechanism of antidepressant activity", J. Clin. Psychiatry 44(5):74–78.
Ferry, L.H. et al., 1992, "Enhancement of smoking cessation using the anti–depressant bupropion hydrochloride" (abstract) Circulation 86:671.
Ferry, L.H. et al., 1994, "Efficacy of bupropion for smpking cessation in non–depressed smokers", J. Addict. Dis. 13:A9.
Fisher, R.S., 1989, "Animal models of the epilepsies", Brain Res. Reviews 14:245–278.
Foote et al., 1984, "Proconvulsant effect of morphine on seizures induced by pentylenetetrazol in the rat", 105:179–184.
Garland et al., 1998, "Pharmacotherapy of adolescent attention deficit hyperactivity disorder: challenges, choices and caveats", J. Psychopharmacology 12(4):385–395.
Goetz et al., 1984, "Bupropion in Parkinson's Disease," 34:1092–4.
Goodnick, P.J., 1994, "Pharmacokinetic optimisation of therapy with newer antidepressants", Clin. Pharmacokinet. 27(4):307–330.
Goodnick, P.J. & Sandoval, R., 1993, "Psychotropic treatment of depression: results of an open trial", J. Clin. Psych. 54(1):13–20.
Green, A.R. & Murray, T.K., 1989, "A simple intravenous infusion method in rodents for determining the potency of anticonvulsants acting through GABAergic mechanisms", J. Pharm. Pharmacol. 41:879–880.
Grimes et al., 1996, "Spontaneous orgasm with the combined use of bupropion and sertraline", Soc. Biol. Psych. 40:1184–1185.
Hsyu, P.H. et al., "Pharmacokinetics of Bupropion and its Metabolites in Cigarette Smokers Versus Nonsmokers", J. Clin. Pharmacology 1997;37:737–743.
Hsyu, P.H. et al., Nov. 10, 1997 Chemical Abstracts 127(19):Abstract No. 257089; Columbus, Ohio.
Kelley, J.L. et al., 1996, "(2S,3S,5R)–2–(3,5–difluorophenyl)–3,5–dimethyl–2–morpholinol: a novel antidepressant agent and selective inhibitor of norepinephrine uptake", J. Med. Chem. 39:347–349.
Ketter, T.A. et al., 1995, "Carbamazepine but not valproate induces bupropion metabolism", J. Clin. Psycopharmacol. 15(5):327–333.
Laizure, S.C. et al., 1985, "Pharmacokinetics of bupropion and its major basic metabolites in normal subjects after a single dose", Clin. Pharmacol. Ther. 38:586–589.
Lief, H.I., 1996, "Bupropion treatment of depression to assist smoking cessation", Am. J. Psychiatry 153(3):442.
Little, K.Y. et al., 1993, "[$^{125}$I]RTI–55 binding to cocaine–sensitive dopaminergic and serotonergic uptake sites in the human brain", J. Neurochem. 61:1996–2006.
P. Martin et al., "Antidepressant Profile of Bupropion and three Metabolites in Mice", Département de Pharmacologie, Faculté de Médicine Pité–alpêtrière, Paris, France, Pharmacopsychiatry 23 (1990) 187–194.
McNamee et al., 1986, "Stimulation of substrate oxidation in rat hepatic mitochondria following pretreatment with appetite modifying drugs", J. Pharm. Pharmacol. 37:147.
Merskey, H., 1965, "The effect of chronic pain upon the response to noxious stimuli by psychiatric patients", J. Psychosom. Res. 8:405.
Michell, G.F. et al., 1989, "Dr, Mitchell and associates reply", Am. J. Psychiatry 146(8):1089.
Michell, G.F. et al., 1989, "Effect of bupropion on chocolate craving", Am. J. Psychiatry 146(1):119–120.
Moret, C. & Brile, M., 1988, "Sensitizing of the response of 5–HT autoreceptors to drugs modifying synaptic availability of 5–HT", 27(1):43–49.

D. Musso et al., "Synthesis and Evaluation of the Anticovulsant Activity of a Series of 2–amino–1–phenyl–1–propanols derived from the Metabolites of the Antidepressant Bupropion", Bioorganic & Medicinal Chemistry Letters, vol. 7, No. 1, pp. 1–6, 1997.

Musso et al., 1993, "Synthesis and evaluation of the antidepressant activity of the enantiomers of bupropion", Chirality 5:495–500.

Neurology, Official Journal of the American Academy of Neurology, Aug. 1984, vol. 34, No. 8.

Nomikos et al., 1992, "Effects of chronic bupropion on interstitial concentrations of dopamine in rat nucleus accumbens and striatum", Neuropsychopharmacology 7(1):7–14.

Nutt, D.J. et al., 1980, "On the measurement in rats of the convulsant effect of drugs and the changes which follow electroconvulsive shock", Neuropharmacology 19:1017–1023.

Nutt, D.J. et al., 1981, "Studies on the postietal rise in seizure threshold", Eur. J. Pharmacol. 71:287–295.

Olsen et al., 1985, "Benzodiazepine/γ–aminobutyric acid receptor deficit in the midbrain of the seizure–susceptible gerbil", PNAS USA 82:6701–6705.

Pearlstein et al., 1997, "Comparison of fluoxetine, bupropion, and placebo in the treatment of premenstrual dysphoric disorder", J. Clin. Psychopharmacol. 17(4):261–266.

Physician's Desk Reference®, pp. 1120–1127 and 1139–1144.

Popli, A.P. et al., 1994, "Antidepressant–associated seizures", J. Clin. Psych. 55(6):267.

Popli, A. et al., 1995, "Bupropion and anticonvulsant drug interactions", Annals of Clin. Psychiatr. 7(2):99–101.

Posner, J. et al., 1985, "The disposition of bupropion and its metabolites in healthy male volunteers after single and multiple doses", Eur. J. Clin. Pharmacol. 29:97–103.

Potter, W.Z. & Manji, H.K., 1990, "Antidepressants, metabolites, and apparent drug resistance", Clin. Neuropharmacol. 13(1):S45–S53.

Rose, J.E., 1996, "Nicotine addiction and treatment", Annu. Rev. Med. 47:493–507.

Rosenstein, D.L. et al., 1993, "Seizures associated with antidepressants: a review", J. Clin. Psychiatry 54(8):289–299.

Rudorfer, M.V. et al., 1994, "Comparative tolerability profiles of the newer versus older antidepressants", Drug Safety 10(1):18–46.

Schroeder, D.H., 1983, "Metabolism and kinetocs of bupropion", J. Clin. Psychiatr. 44(5);79–81.

Schroedger, D.H. et al., 1979, "The isolation and identification of some basic urinary metablites of bupropion—HCL in man", The Pharmacologiest 21(3):191.

SCRIP Bupropion Sustained Release (SR) for Smoking Cessation, Dec. 18, 1996.

SCRIP Itraconazole for pulse dosing of onychomycosis, Dec. 18, 1996.

Scrip's New Product Review, No. 50 Bupropion, Aug., 1990, PJB Publications.

Stathis, M. et al., 1995, "Rate of binding of various inhibitors at the dopamine transporter in vivo", Psychopharmacol. 119:376–384.

Storrow, A.B., 1994, "Bupropion overdose and seizure", Am. J. Emerg. Med. 12:183–184.

Suckow, R.F. et al., 1986, "Pharmacokinetics of bupropion and metabolites in plasma and brain of rats, mice, and guinea pigs", Drug Metab. Disposit. 14(6):692–697.

Suckow, R.F. et al., 1997, "Enantiomeric determination of the phenylmorpholinol metabolite of bupropion in human plasma using coupled achiral–chiral liquid chromatography", Biomedical Chromatog 11:174–179.

Sulser, F., 1983, "Molecular mechanisms in antidepressant action", Psychopharmacol. Bull. 19(3):300.

Sweet, R.A. et al., 1995, "Pharmacokinetics of single– and multiple– dose bupropion in elderly patients with depression", J. Clin. Pharmacol. 35:876–884.

B. Testa et al., Racemates Versus Enatiomers in Drug Development: Dogmatism or Pragmatism?, Department of Medicinal Chemistry, School of Pharmacy, University of Washington, Seattle, Washington 98195 (W.F.T.), Chirality 2:129–133 (1990).

Vassout, A. et al., 1993, "Regulation of dopamine receptors by bupropion: compariosn with antidepressants and CNS stimulants", J. Receptor Res. 13(1–4):341–354.

Ward, R. et al., 1971, "Asymmetric audiogenic seizures in mice: a possible analogue of focal epilepsy", Brain Res. 31:207–210.

Ward, N.G., 1990, *The Management of Pain*, Second Edition, vol. 1, Chapter 18, (eds.) Bonica, J.J. pp. 310–319.

Welch, R.M. et al., 1987, "Pharmacological significance of the species differences in bupropion metabolism", Nenobiotica 17(3):287–298.

Wilen, S.H., 1972, *Tables of Resolving Agents and Optical Resolutions*, Univ. of Notre Dame Press, Notre Dame, IN.

G. Wright et al., "Bupropion in the Long–Term Treatment of Cyclic Mood Disorders: Mood Stabilizing Effects", Genessee Psychiatric Clinic, Flint, Michigan, J. Clin. Psychiatry 46:1, pp. 22–25, Jan. 1985.

Zarrindast et al., 1988, "Anorectic and behavioral effects of bupropion", Gen. Pharmacology 19(2):201–204.

* cited by examiner

METHODS AND COMPOSITIONS FOR AIDING IN SMOKING CESSATION AND FOR TREATING PAIN AND OTHER DISORDERS USING OPTICALLY PURE (+)-BUPROPION

This application is a Divisional of 09/238,984 filed Jan. 28, 1999 which claims benefit of 60/072,933 filed Jan. 29, 1998.

1. FIELD OF THE INVENTION

This invention relates to methods and pharmaceutical compositions for aiding smoking cessation, treating nicotine addiction, and pain, including chronic pain, neuropathetic pain and reflex sympathetic dystrophy, and other disorders.

2. BACKGROUND OF THE INVENTION

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 16 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer was a potent teratogen.

Bupropion is available only as a racemic mixture. That is, bupropion is available as an approximate 50/50 mixture of optical isomers, called enantiomers. The racemic mixture of bupropion which is commercially available is administered as a hydrochloride salt. In addition, European Patent Application No. 84101070.5 published Sep. 12, 1984 discloses the benefits of bupropion maleate over bupropion hydrochloride. The racemic mixture of bupropion is available as Wellbutrin® and Wellbutrin SR® for the treatment of depression and Zyban® to achieve smoking cessation, respectively.

Bupropion is used primarily in the treatment of depression, which along with mania, falls under the heading of affective disorders. Particularly, racemic bupropion is used in patients who do not respond to, or cannot tolerate other antidepressants, such as the tricyclic agents or monoamine oxidase inhibitors. Additionally, the racemic mixture of bupropion is useful in the management of patients with bipolar and schizo-affective disorder, attention-deficit disorder, psycho-sexual dysfunction, bulimia and other eating disorders, and Parkinson's disease.

Affective disorders, including major depression, and the bipolar, manic-depressive illness, are characterized by changes in mood as the primary clinical manifestation. Major depression, the most common of the significant mental illnesses, is characterized by feelings of intense sadness, and despair, mental slowing and loss of concentration, pessimistic worry, agitation, and self-deprecation. Physical changes can also occur, including insomnia, anorexia, and weight loss, decreased energy and libido, and disruption of hormonal circadian rhythms.

Through an as yet unknown mechanism of action, bupropion has been demonstrated to be an effective treatment in depression in short-term and longer duration clinical studies. The racemic mixture of bupropion has been reported to have antidepressant activity equal to amitriptyline, the tricyclic antidepressant, with fewer anticholinergic, sedative and cardiovascular side effects than with amitriptyline.

As mentioned above, racemic bupropion is used primarily in the treatment of depression and in smoking cessation and is available for these indications in the United States as Wellbutrin® and WellbutrinSR® (for depression) and Zyban® for smoking cessation), respectively (Physicians Desk Reference 1998 52nd edition, pp. 1120–1127 and 1139–1144). Studies regarding the mechanism of bupropion's antidepressant activity have shown that bupropion is an atypical antidepressant that demonstrates a significant and unusual pattern of noradrenergic activity including some but not all of the effects seen after chronic administration of reuptake inhibitors. Bupropion produces a unique spectrum of biochemical effects that differ significantly from those produced by other antidepressants. However, the exact mechanism by which bupropion produces its antidepressant effects is still not completely understood. See Ascher, J. A., et al., 1995, *J. Clin. Psychiatry* 56:395–401.

The persistence of cigarette smoking despite widespread public awareness of the adverse health effects in large part results from an underlying addiction to nicotine. Nicotine is a highly addictive substance, which has been said to be as addictive as heroin. A number of nicotinic receptor subtypes have been discovered, which differ in both regional distribution in the nervous system and functional significance. Nicotine binds to these nicotine receptors to open a cation channel that causes depolarization and cell firing. Nicotine has been shown to increase neuronal firing rates in ventral tegmental area dopamine cells, and nicotine enhances dopamine release in striatal areas, including the nucleus accumbeus, which is implicated in drug reinforcement. Thus, it is known that nicotine activates the dopamine reward system. This reinforcement of activation of the dopamine reward system leads to nicotine addiction and difficulty in smoking cessation.

Bupropion inhibits dopamine reuptake, although this inhibition occurs at doses higher than needed for antidepressant activity. Racemic bupropion has been reported to increase success rates in smoking cessation treatment. Rose, J. E., 1996, "Nicotine Addiction and Treatment," *Annu. Rev. Med.* 47:493–507; Ferry, L. H. et al., 1994, "Efficacy of Bupropion for Smoking Cessation in Non-Depressed Smokers," *J. Addict. Dis.* 13:A9. However, one researcher reported a case in which the cycle of smoking cessation, associated with weight gain, followed by depression and resumption of smoking was interrupted by the use of bupropion as a preventative measure. Lief, H. I., March 1996, "Bupropion Treatment of Depression to Assist Smoking Cessation," *Am. J. Psychiatry* 153:3, p. 442. In this case, it was thought that the administration of racemic bupropion had an indirect effect in preventing smoking resumption by treating the patient's depression, which had been caused by weight gain associated with smoking cessation. Cf. Ferry, L. H. et al., 1992, "Enhancement of Smoking Cessation Using the Anti-Depressant Bupropion Hydrochloride" (abstract), *Circulation* 1992, 86:671; Ferry, L. H. et al., 1994, "Evaluation of Bupropion Versus Placebo for Treatment of Nicotine Dependence," New Research Program and Abstracts, 147th Annual Meeting of the American Psychiatric Association, Wash., D.C., APA, pp. 199–200.

Patients who suffer from chronic pain may also experience depression. In studies on patients having chronic pain, the incidence of clinical depression ranges from 22 to 78%. Similarly, in studies on depression patients, the frequency of persistent pain complaints ranges from 30 to 100%. Bonica, J. J., *The Management of Pain*, Second Edition, Vol. I, Chapter 18, pp. 310–319 (1990). In comparison, the occurrence of major depression in the general population is about 4 or 5% with about 3% of men and 6% of women being depressed at any given time. Thus, it is generally believed that the occurrence of depression is greater in patients with chronic pain than in the normal population, but there is no consensus on the extent to which pain and depression may coexist.

In addition, pain and depression may coexist more often in certain clinical populations, such as women, perhaps because of the higher prevalence of depression in women in general. The most prevalent form of chronic pain syndromes associated with depression is chronic persistent headache.

There are presently several theories which attempt to explain why depression and pain frequently coexist; some theories hypothesize that depression comes first and others that pain comes first. See, e.g., Merskey, H., 1965, "The Effect of Chronic Pain Upon the Response to Noxious Stimuli by Psychiatric Patients," *J. Psychosom. Res.* 8:405. For example, one theory indicates that since anxiety is frequently associated with depression, and anxiety can potentially increase muscle tension, anxiety can therefore create pain.

Other theories link the connection between pain and depression to several biogenic amines including serotonin, norepinephrine, and dopamine. These compounds have been reported to play a role in the modulation of pain in animals. In addition, abnormalities in biogenic amine function, particularly nor-pinephrine and serotonin, have been hypothesized to play a role in the onset and maintenance of depression. According to these theories, a shared disturbance in noradrenergic and/or serotonergic function might link chronic pain and depression. See Charney D. S., and Heninger, G. R., 1983, "Monoamine Receptor Sensitivity and Depression: Clinical Studies of Antidepressant Effects on Serotonin and Noradrenergic Function," *Psychopharmacol. Bull.*, 19(3):490; Sulser, F., 1983, "Molecular Mechanisms in Antidepressant Action," *Psychopharmacol. Bull.*, 19(3):300.

Pain is generally considered by physicians to have either an organic or a functional psychologic basis. Pain having an organic basis is demonstrated by a specific lesion with well-defined characteristics of pain. However, it has also been found that there are biochemical (e.g. serotonergic) abnormalities that exist without specific lesions, which are manifested by dull, diffuse pains. The absence of a defined lesion does not mean that patients with chronic pain do not have something physically wrong with them. The abnormality might only be found at the molecular level.

Chronic fatigue syndrome (CFS) is a disorder characterized by fatigue of an incapacitating nature lasting for at least six months. Symptoms of chronic fatigue syndrome include, but are not limited to, mild fever or chills, sore throats, painful lymph nodes, unexplained general muscle weakness, myalgias, prolonged generalized fatigue after exercise previously tolerated, generalized headaches, migratory arthralgias, neuropsychologic complaints, sleep disturbance, and description of a main symptom complex developing over a few hours to a few days.

Physical signs of chronic fatigue syndrome include low-grade fevers, nonexudative pharyngitis and palpable or tender anterior or posterior cervical or axillary lymph nodes. See Goodnick, P. J. and Sandoval, R., January 1993, "Psychotropic Treatment of Chronic Fatigue Syndrome and Related Disorders," *J. Clin. Psychiatry* 54(1):13–20.

Fibromyalgia is a disorder related to chronic fatigue syndrome. However, in contrast to chronic fatigue syndrome, the major symptoms of fibromyalgia do not include fatigue. Instead, fibromyalgia is characterized by generalized aches or stiffness involving three or more anatomic sites for at least 3 months and at least six typical and reproducible tender points. Minor symptoms of fibromyalgia include fatigue, headache, sleep disturbance, neuropsychiatric symptoms, subjective joint swelling, numbness, irritable bowel syndrome, and modulation of symptoms by activity, weather and stress. Despite the differences in their definitions, patients with either fibromyalgia or chronic fatigue syndrome share many symptoms and epidemiologic factors. See Goodnick, P. J. and Sandoval, R.

Seasonal affective disorders (SADs) are clinically significant disturbances of mood occurring in relationship to a change in season. Winter depression, the most widely recognized form of SAD, is characterized by the onset of depression in the fall or winter followed by spontaneous recovery in the spring. While phototherapy is the most widely studied and recognized treatment for SAD, one study has suggested that racemic bupropion is an effective treatment for winter depression. Dilsaver, S. C., et al., July 1992, "The Efficacy of Bupropion in Winter Depression: Results of an Open Trial," *J. Clin. Psychiatry* 53(7):252–255.

The racemic mixture of bupropion, in addition to its use in the treatment of depression, has been shown to have a wide spectrum of action which includes:

Treatment of the effects of ethanol (U.S. Pat. No. 4,393,078)

Treatment of Tardine Dyskinesia (U.S. Pat. No. 4,425,363)

Treatment of Minimal Brain Dysfunction (U.S. Pat. No. 4,435,449)

Treatment of amelioration of prostate hypertrophy and sexual dysfunction (U.S. Pat. No. 4,835,147)

Treatment of psychostimulant addiction (U.S. Pat. No. 4,935,429)

Treatment of Psychosexual dysfunction (U.S. Pat. No. 4,507,323)

Methods of reducing cholesterol (U.S. Pat. No. 4,438,138)

Methods of assisting weight loss (U.S. Pat. No. 4,895,845)

The racemic mixture of bupropion has been shown to have certain advantages over other antidepressant drugs. For example, bupropion does not inhibit monoamine oxidase, or block the reuptake of serotonin. At therapeutic concentrations, the compound presumably does not bind to adrenergic, dopamine, GABA, histamine, muscarinic, serotonin, or imipramine binding sites. While its specific neurochemical antidepressant action is unknown, it does have a relatively weak effect on blocking the reuptake of dopamine.

While the racemic mixture of bupropion has advantages, it also has disadvantages. Among these disadvantages are adverse effects in addition to those described above. The most serious adverse effect associated with the racemic mixture of bupropion is the incidence of seizures. In addition, other frequently reported adverse effects associated with the use of racemic bupropion include nausea, vomiting, excitement, blurred vision, agitation, restlessness, postural tremor, and some hallucinations/confusional states with the potential for abuse. Other adverse or side effects associated with the racemic mixture of bupropion include but are not limited to anxiety, insomnia, headaches and/or migraines, dry mouth, constipation, tremor, sleeping disturbances, dermatologic problems (e.g., rashes), neuropsychiatric signs and symptoms (e.g., delusions and paranoia), and weight loss or gain. See, The Physician's Desk Reference® (1998). These effects are dose limiting in a number of patients. In Parkinsonian patients, the adverse effects can be the particular toxicity of the racemic mixture of bupropion or the result of a drug interaction (as most patients were receiving concomitant levodopa).

Thus, it is desirable to find a compound with the advantages of the racemic mixture of bupropion without the above-described disadvantages. In particular, there is a need for a compound which is effective for the treatment of pain and disorders such as, smoking and nicotine addiction, without the above-described disadvantages and adverse effects associated with the administration of racemic bupropion.

3. SUMMARY OF THE INVENTION

The active compound of compositions and methods disclosed herein is an optical isomer of the racemic compound bupropion which is described in U.S. Pat. Nos. 3,819,706 and 3,885,046. Chemically, this isomer is (+)-2-(tertbutylamino)-3'-chloropropiophenone or (+)-1-(3-chlorophenyl)-2[(1,1-dimethyl-ethyl)amino]-1-propanone. This isomer will hereinafter be referred to as "(+)-bupropion," which also includes the substantially optically pure (+)-bupropion isomer.

It has been discovered that optically pure (+)-bupropion is effective in aiding or achieving smoking cessation while avoiding adverse effects associated with the administration of racemic bupropion. Another embodiment of the present invention relates to the treatment of smoking or nicotine addiction by administration of optically pure (+)-bupropion or a pharmaceutically acceptable salt thereof.

It has also been discovered that-the optically pure (+)-isomer of bupropion is effective for the treatment of pain, including chronic pain, neuropathic pain, pain associated with depression and reflex sympathetic dystrophy, while avoiding adverse effects, including, but not limited to, seizures, agitation, dry mouth, insomnia, headache/migraine, nausea, vomiting, dizziness, tachycardia, constipation, and tremor associated with the administration of the racemic mixture of bupropion. It has further been discovered that optically pure (+)-bupropion is useful in the treatment of chronic disorders, including narcolepsy, chronic fatigue syndrome, fibromyalgia, seasonal affective disorder and premenstrual syndrome, (or premenstrual dysphoric disorder) while avoiding adverse effects, such as those described above, associated with the administration of the racemic mixture of bupropion.

Thus, the present invention encompasses methods for treating the above-described conditions in a human while avoiding adverse effects that are associated with the racemic mixture of bupropion, by administering the optically pure (+)-isomer of bupropion or a pharmaceutically acceptable salt thereof, to said human. The present invention also relates to compositions comprising optically pure (+)-bupropion.

4. DETAILED DESCRIPTION OF THE INVENTION

The present invention encompasses a method for aiding in smoking cessation in a human, which comprises administering to a human who smokes a therapeutically effective amount of (+)-bupropion, or a pharmaceutically acceptable salt thereof, substantially free of its (−)-stereoisomer. Thus, the invention encompasses the use of optically pure (+)-bupropion to achieve smoking cessation or a reduction in smoking.

The present invention further encompasses a method for aiding smoking cessation while avoiding the concomitant liability of adverse effects associated with the administration of racemic bupropion, which comprises administering to a human who smokes a therapeutically effective amount of (+)-bupropion, or a pharmaceutically acceptable salt thereof, substantially free of its (−)-stereoisomer, said amount being sufficient to achieve smoking cessation or a reduction in smoking, but insufficient to cause adverse effects associated with the administration of racemic bupropion.

The present invention further encompasses a method of treating nicotine addiction in a human, which comprises administering to said human suffering from nicotine addiction a therapeutically effective amount of (+)-bupropion, or a pharmaceutically acceptable salt thereof, substantially free of its (−)-stereoisomer. Nicotine addiction refers to nicotine addiction in all known forms, such as smoking cigarettes, cigars, or pipes and chewing tobacco.

The present invention further encompasses a method of treating nicotine addiction in a human while avoiding the concomitant liability of adverse effects associated with the administration of racemic bupropion, which comprises administering to said human suffering from nicotine addiction a therapeutically effective amount of (+)-bupropion, or a pharmaceutically acceptable salt thereof, substantially free of its (−)-stereoisomer, said amount being sufficient to alleviate said addiction, but insufficient to cause adverse effects associated with administration of racemic bupropion.

Addiction to nicotine or tobacco includes addiction to smoking cigarettes, cigars and/or pipes, and addiction to chewing tobacco.

The present invention further encompasses a method for treating weight gain associated with smoking cessation in a human, which comprises administering to said human suffering from weight gain associated with smoking cessation, a therapeutically effective amount of (+)-bupropion, or a pharmaceutically acceptable salt thereof, substantially free of its (−)-stereoisomer.

The present invention further encompasses a method for treating weight gain associated with smoking cessation in a human while avoiding the concomitant liability of adverse effects associated with the administration of racemic bupropion, which comprises administering to said human suffering from weight gain associated with smoking cessation, a therapeutically effective amount of (+)-bupropion or a pharmaceutically acceptable salt thereof, substantially free of its (−)-stereoisomer, said amount being sufficient to achieve weight loss, but insufficient to cause adverse effects associated with administration of racemic bupropion.

The present invention is also directed to a method of treating pain in a human which-comprises administering to said human in need of treatment for pain a therapeutically effective amount of (+)-bupropion, or a pharmaceutically acceptable salt thereof, substantially free of its (−)-stereoisomer, said amount being sufficient to alleviate pain.

In addition, the present invention encompasses a method of treating pain in a human while avoiding the concomitant liability of adverse effects associated with the administration of racemic bupropion, which comprises administering to said human in need of treatment for pain, a therapeutically effective amount of (+)-bupropion or a pharmaceutically acceptable salt thereof, substantially free of its (−)-stereoisomer, said amount being sufficient to alleviate pain, but insufficient to cause adverse effects associated with racemic bupropion. The types of pain which may be treated according to the methods of the present invention include, but are not limited, chronic pain, pain associated with depression, neuropathic pain, persistent headache, and reflex sympathetic dystrophy.

The present invention also encompasses a composition for the treatment of pain in a human which comprises a therapeutically effective amount of (+)-bupropion, or a pharmaceutically acceptable salt thereof, substantially free of its (−)-stereoisomer, and a pharmaceutically acceptable carrier. Preferred pharmaceutical compositions are those which have a means for controlled, and/or sustained release of the active ingredient, (+)-bupropion.

The present invention further encompasses a method of treating a chronic disorder in a human, which comprises administering to said human suffering from a chronic disorder a therapeutically effective amount of (+)-bupropion, or a pharmaceutically acceptable salt thereof, substantially free of its (−)-stereoisomer.

The present invention further encompasses a method of treating a chronic disorder in a human while avoiding the concomitant liability of adverse effects associated with the administration of racemic bupropion, which comprises administering to said human suffering from a chronic disorder a therapeutically effective amount of (+)-bupropion, or a pharmaceutically acceptable salt thereof, substantially free of its (−)-stereoisomer, said amount being sufficient to alleviate said chronic disorder, but insufficient to cause adverse effects associated with administration of racemic bupropion.

The term "chronic disorder" as used herein shall mean disorders including, but not limited to, narcolepsy, chronic fatigue syndrome, seasonal affective disorder, fibromyalgia and premenstrual syndrome (or premenstrual dysphoric disorder).

The racemic mixture of bupropion (i.e., an approximately 50%—50% mixture of its two enantiomers) has been reported to be useful in reducing certain types of pain.

Davidson, J. R. and France, R. D., August 1994, "Bupropion in Chronic Low Back Pain," *J. Clin. Psychiatry* 55(8):362. Although racemic bupropion may provide therapy and/or reduction of symptoms in a variety of conditions and disorders, this racemic mixture, while offering the expectation of efficacy, causes a broad range of adverse effects. According to the present invention, utilizing the optically pure (+)-isomer of bupropion results in clearer dose-related definitions of efficacy, diminished adverse effects, and accordingly an improved therapeutic index. It is therefore, more desirable to use the (+)-isomer of bupropion to treat the conditions described herein.

The term "adverse effects" includes, but is not limited to, seizures, dry mouth, insomnia, dizziness, restlessness, anxiety, agitation, headache/migraine, nausea/vomiting, constipation, tremor, delusions, tachycardia, hallucinations, psychotic episodes, blurred vision, confusion, paranoia, rashes and sleep disturbances.

The term "substantially free of the (−)-stereoisomer" as used herein means that the composition contains a greater proportion of the (+)-isomer of bupropion in relation to the (−)-isomer of bupropion. In a preferred embodiment the term "substantially free of its (−)-stereoisomer" as used herein means that the composition contains at least 90% by weight of (+)-bupropion and 10% by weight or less of (−)-bupropion; in a more preferred embodiment at least 95% (+)-bupropion and 5% by weight or less of its (−)-isomer. These percentages are based on the total amount of bupropion present in the composition. In the most-preferred embodiment the term "substantially free of its (−)-stereoisomer" means that the composition contains approximately 99% by weight of (+)-bupropion, and 1% or less of (−)-bupropion. In another preferred embodiment, the term "substantially free of its (−)-stereoisomer" as used herein means that the composition contains greater than 99% by weight of the (+)-isomer of bupropion, again based on the total amount of bupropion present. The terms "substantially optically pure (+)-isomer of bupropion," "optically pure (+)-isomer of bupropion," "optically pure (+)-bupropion" and "(+)-isomer of bupropion" are also encompassed by the above-described amounts.

4.1. SYNTHESIS OF OPTICALLY PURE (+)-BUPROPION

The synthesis of the (+)-isomer of bupropion may start from readily available 3-chloropropiophenone (1). Reaction of (1) with a (2S,3S)-(−)-dialkyl tartrate such as (−)-dimethyl or diethyl tartrate in the presence of an acid catalyst such as methanesulfonic acid gives the chiral acetal (2) according to Castaldi (G. Castaldi, et al., *J. Org. Chem.* 1987, 52:3018). Steroselective bromination with bromine in carbon tetrachloride (or alternatively ethyl acetate) then produces the corresponding bromoacetal (3) as the major product according to the above-referenced procedure developed by Castaldi and co-workers. The bromoacetal (3) is purified by column chromatography to yield the optically pure bromoacetal (3) which is then hydrolyzed in the presence of an acid to afford the bromoketone (4). Treatment of the bromoketone (4) with tert-butylamine, followed by reaction with anhydrous hydrogen chloride, then produces optically pure (+)-bupropion hydrochloride (5) after recrystallization. See the scheme below.

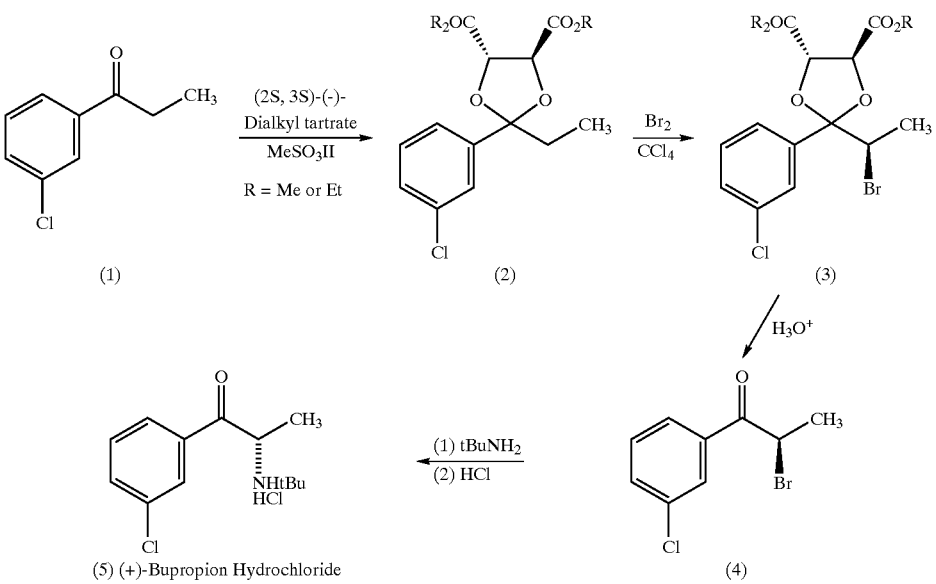

(5) (+)-Bupropion Hydrochloride

Alternatively, the optically pure (+)-isomer of bupropion can be prepared according to the procedures reported by Musso et al., 1993, "Synthesis and Evaluation of the Antidepressant Activity of the Enantiomers of Bupropion," *Chirality* 5:495–500, which is hereby incorporated by reference in its entirety.

In addition to the above-described methods, the stereoisomers of bupropion may be obtained by resolutions of a mixture of enantiomers of bupropion using conventional means such as an optically active resolving agent; see, for example, "Stereochemistry of Carbon Compounds", by E. L. Eliel (McGraw-Hill, NY, 1962), and S. H. Wilen, p. 268 in "Tables of Resolving Agents and Optical Resolutions" (E. L. Eliel, Ed., Univ. of Notre Dame Press, Notre Dame, Ind., 1972).

The magnitude of a prophylactic or therapeutic dose of (+)-bupropion in the acute or chronic management of disease (or disorders) will vary with the severity of the condition to be treated and its route of administration. The dose and dose frequency will also vary according to the age, weight and response of the individual patient. In general, the recommended daily dose range for the conditions described herein lies within the range of from about 10 mg to about 750 mg per day, generally divided equally into doses given two to four times a day. Preferably, a daily dose range should be between 50 mg and 600 mg per day, usually divided equally into a two to four times a day dosing. Most preferably, a daily dose range should be between 60 mg and 450 mg per day, usually divided equally into a two to four times a day dosing. It may be necessary to use dosages outside these ranges in some cases. The physician will know how to increase, decrease or interrupt treatment based upon patient response. For use in aiding in smoking cessation or in treating nicotine addiction, the physician will generally prescribe the period of treatment and frequency of dose of (+)-bupropion on a patient-by-patient basis. In general, however, treatment with (+)-bupropion may be carried out for a period of 2 weeks to 6 months, and preferably from 7 weeks to 12 weeks. The various terms described above such as "said amount being sufficient to alleviate pain", "said amount being sufficient to alleviate said addiction", "therapeutically effective amount", etc., are encompassed by the above-described dosage amounts and dose frequency schedule.

Any suitable route of administration may be employed for providing the patient with an effective dosage of (+)-bupropion. For example, oral, rectal, parenteral, transdermal, subcutaneous, intramuscular, intrathecal and the like may be employed as appropriate. Dosage forms include tablets, coated tablets, caplets, capsules, troches, dispersions, suspensions, solutions, patches and the like, including sustained release formulations well known in the art. See, e.g. Remington's Pharmaceutical Sciences (1995) and the Physician's Desk Reference® (1998).

The pharmaceutical compositions of the present invention comprise the (+)-isomer of bupropion as active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic acids including inorganic acids and organic acids.

Since the compound of the present invention is basic, salts may be prepared from pharmaceutically acceptable non-toxic acids including inorganic and organic acids. Such acids include maleic, acetic, benzene-sulfonic (besylate), benzoic, camphorsulfonic, citric, ethenesulfonic, fumaric, gluconic, glutamic, hydrobromaic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are hydrobromic, hydrochloric, maleic, phosphoric, and sulfuric acids.

The compositions include compositions suitable for oral, rectal, and parenteral administration (including subcutaneous, intramuscular, intrathecal and intravenous), although the most suitable route in any given case will depend on the nature and severity of the condition being treated. The most preferred route of the present invention is the oral route. They may be conveniently presented in unit dosage form and prepared by any of the methods well-known in the art of pharmacy.

In the case where an oral composition is employed, a suitable dosage range for use is, e.g., from about 10 mg to about 750 mg per day, generally divided equally into a two to four times a day dosing, preferably from about 50 mg to about 600 mg per day, generally divided equally into a two to four times a day dosing and most preferably from about 60 mg to about 450 mg per day, generally divided equally into a two to four times a day dosing. Patients may be upward titrated from below to within this dose range to achieve satisfactory control of symptoms as appropriate.

In practical use, (+)-bupropion can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous injections or infusions). In preparing the compositions for oral dosage form, any of the usual pharmaceutical media may be employed, for example, water, glycols, oils, alcohols, flavoring agents, preservatives, coloring agents and the like in the case of oral liquid preparations, for example, suspensions, elixirs and solutions; or aerosols; or carriers such as starches, sugars, microcrystalline cellulose, stabilizers, diluents, granulating agents, lubricants, binders, fillers, disintegrating agents and the like in the case of oral solid preparations such as, powders, capsules and tablets, with the solid oral preparations being preferred over the liquid preparations. The preferred solid oral preparation is tablets. The most preferred solid oral preparation is coated tablets. Because of their ease of administration tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of the present invention may also be administered by controlled release or sustained release means and/or delivery devices such as those described in U.S. Pat. Nos. 3,845,770; 3,916,899; 3,536,809; 3,598,123; 3,630,200, 4,008,719, 4,687,660, and 4,769,027, the disclosures of which are hereby incorporated by reference. Preferred controlled release or sustained release tablets for use with (+)-bupropion are described in U.S. Pat. No. 5,427,798 which is incorporated herein by reference.

Pharmaceutical stabilizers may also be used to stabilize compositions containing (+)-bupropion or salts thereof; acceptable stabilizers include but are not limited to L-cysteine hydrochloride, glycine hydrochloride, malic acid, sodium metabisulfite, citric acid, tartaric acid and L-cysteine dihydrochloride. See, e.g. U.S. Pat. No. 5,358,970 which is incorporated herein by reference.

Pharmaceutical compositions of the present invention suitable for oral administration may be presented as discrete units such as capsules, cachets, or tablets or aerosol sprays, each containing a predetermined amount of the active ingredient, as a powder or granules or as a solution or a suspension in an aqueous liquid, a non-aqueous liquid, an oil-in-water emulsion, or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine the active ingredient in a free-flowing form such as powder or granules, optionally mixed with one or more of a binder, filler, stabilizer, lubricant, inert diluent, and/or surface active or dispersing agent. Molded tablets may be made by molding in a suitable machine a mixture of the powdered compound moistened with an inert liquid diluent. Desirably, each tablet contains from about 10 mg to about 250 mg of the active ingredient, and each cachet or capsule contains from about 10 mg to about 250 mg of the active ingredient. In a preferred embodiment, the tablet, cachet or capsule contains one of four dosages: about 50 mg, about 75 mg, about 100 mg and about 150 mg of active ingredient.

The invention is further defined by reference to the following examples describing in detail the preparation of the compound and compositions of the present invention. It will be apparent to those skilled in the art that many modifications, both to materials and methods, may be practiced without departing from the purpose and interest of this invention.

All temperatures are in degrees Celsius.

5. EXAMPLES

5.1. Example 1

ORAL FORMULATION
Coated Tablets:

| Formula | Quantity per Tablet (mg.) |
| --- | --- |
| (+) −bupropion | 75 |
| Lactose | 125 |
| Corn Starch | 5.0 |
| Water (per thousand Tablets) | 30.0 ml* |
| Magnesium Stearate | 0.5 |
| Corn Starch | 25.0 |

*The water evaporates during manufacture.

The active ingredient is blended with the lactose until a uniform blend is formed. The smaller quantity of corn starch is blended with a suitable quantity of water to form a corn starch paste. This is then mixed with said uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous techniques.

5.2. Example 2

ORAL FORMULATION
Capsules:

| Formula | Quantity per capsule in mg. | | |
| --- | --- | --- | --- |
| | A | B | C |
| Active ingredient (+) −bupropion | 25 | 50 | 75 |
| Lactose | 149.5 | 124.5 | 374 |

-continued

ORAL FORMULATION
Capsules:

| Formula | Quantity per capsule in mg. | | |
|---|---|---|---|
| | A | B | C |
| Corn Starch | 25 | 25 | 50 |
| Magnesium Stearate | 0.5 | 0.5 | 1.0 |
| Compression Weight | 200.0 | 200.0 | 500.0 |

The active ingredient, (+)-bupropion, lactose, and corn starch are blended until uniform; then the magnesium stearate is blended into the resulting powder. The resulting mixture is encapsulated into suitably sized two-piece hard gelatin capsules.

5.3. Example 3

ORAL FORMULATION
Tablets

| Formula | Quantity per Tablet in mg. | | |
|---|---|---|---|
| | A | B | C |
| Active ingredient, (+)-bupropion | 20 | 40 | 100 |
| lactose BP | 134.5 | 114.5 | 309.0 |
| starch BP | 30.0 | 30.0 | 60.0 |
| Pregelatinized Maize Starch BP | 15.0 | 15.0 | 30.0 |
| magnesium stearate | 0.5 | 0.5 | 1.0 |
| Compression Weight | 200.0 | 200.0 | 500.0 |

The active ingredient is sieved through a suitable sieve and blended with lactose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to lactose or the compression weight and using punches to suit.

5.4. Example 4

Sustained Release Formulation (Tablet)

| FORMULA | QUANTITY PER TABLET (mg) |
|---|---|
| (+) –bupropion hydrochloride | 100 |
| Contramid ® crosslinked amylose | 98.8 |
| Cysteine hydrochloride | 7.5 |
| Magnesium stearate | 1.2 |

(+)-Bupropion Hydrochloride is formulated using Contramid® (Labopharm, Inc, Quebec) technology. The formulation is prepared by blending the ingredients above (dry) and compressing into tablets. Alternatively, the ingredients can be formulated using wet granulation technology known in the art. (See Example 1).

5.5. Example 5

Sustained Release Formulation (Tablet)

| FORMULA | QUANTITY PER TABLET (mg) |
|---|---|
| Contramid ® crosslinked amylose | 98.8 |
| Cysteine hydrochloride | 7.5 |
| (+) –bupropion hydrochloride | 75.0 |
| Magnesium stearate | 1.2 |

(+)-Bupropion Hydrochloride is formulated using Contramid® (Labopharm, Inc, Quebec), technology. The formulation is prepared-by blending the ingredients above (dry) and compressing into tablets. Alternatively, the ingredients can be formulated using wet granulation technology known in the art. (See Example 1).

5.6. Example 6

| FORMULA | QUANTITY PER TABLET (mg) |
|---|---|
| (+) –bupropion hydrochloride | 150 |
| Diffutab ® hydrophilic polymer mixture | 100 |
| Microcrystalline cellulose | 100 |
| Cysteine hydrochloride | 7.5 |
| Magnesium stearate | 4 |

(+)-Bupropion Hydrochloride is formulated using Diffutab® (Eurand, Microencapsulation, S.A. of Switzerland) technology. The formulation components are dry blended and directly compressed into tablets or formulated using wet granulation technology.

5.7. Example 7

Seizure Model (+)-Bupropion can be tested in a rodent model of seizure threshold such as that described by Green and Murray, 1989, "A Simple Intravenous Infusion Method in Rodents for Determining The Potency of Anticonvulsants Acting Through GABAergic Mechanisms", *J. Pharm. Pharmacol.* 41:879–880. See also Nutt, D. J., et al. 1980, "On the Measurement in Rats of the Convulsant Effect of Drugs and the Changes Which Follow Electroconvulsive Shock," *Neuropharmacology* 19:1017–1023; Nutt, D. J., et al. 1981, "Studies on the Postietal Rise in Seizure Threshold," *Eur. J. Pharmacol.* 71:287–295. In such tests, a group of rats is lightly restrained and a solution of a convulsant drug such as pentetrazol, is infused via a needle inserted into a tail vein of each rat at a predetermined concentration such as 10 mg/mL, and at a predetermined rate, such as of 2.6 mL/min. The rate of infusion gives a clear end point for seizure threshold. The time of infusion of the convulsant drug required to produce the first myoclonic twitch (which occurs with the first EEG abnormality) is recorded and doses required to produce the seizure calculated. Seizure threshold is expressed as mg/kg and can be calculated using the following formula.

$$\frac{\text{Infusion rate (mL/min)} \times \text{drug concentration (mg/mL)} \times \text{time to twitch (sec)}}{60 \times \text{rat weight (kg)}}$$

(+)-Bupropion, racemic bupropion and other substances tested are administered by IP or IV injection at a preselected time, for example 15 minutes before the determination of seizure threshold.

5.8. Example 8

Pain: Writing Model

Phenylquinone Writhing Assay in Mice

The antiphenylquinone writhing test is a standard procedure for detecting and comparing analgesic activity in laboratory animals, and generally correlates well with human efficacy. In response to an injected, locally irritating solution, such as phenyl-p-benzoquinone, the animals have cramps ("writhings") that are inhibited by analgesic or pain-relieving agents.

Mice are first dosed with at least two dose levels each of (+)-bupropion, racemic bupropion and other test substances including one or more control substances such as aspirin. The mice are then challenged with an irritating agent, such as phenyl-p-benzoquinone, given intraperitoneally and observed for the characteristic patterns of stretch-writhing syndrome, including torsion of the abdomen and thorax, drawing the hind legs close to the body and raising the heels of the hind feet-off the floor of the housing. Lack of writhing constitutes a positive response. The degree of analgesic protection can be calculated on the basis of suppression of writhing relative to control animals run on the same day. Time response data are also obtained. Observations are made early enough post-dosing to detect differences in onset.

5.9. Example 9

Other models may be used to test activity of (+)-bupropion, some of which are discussed below, and as described in Bannon, A. W. et al., Jan. 2, 1998, "Broad Spectrum, Non-opioid Analgesic Activity By Selective Modulation of Neuronal Nicotinic Acetylcholine Receptors, *Science* 279:77–81.

Formalin Test

The formalin test is an animal model for persistent chemical pain. In the formalin test, the second phase of the biphasic nociceptive response is thought to be mediated, in part, by a sensitization of neuronal function at the level of the spinal cord and reflect the clinical observation of hyperalgesia associated with tissue injury. The method used for the formalin test is based on a modified version of a previously published method [D. Dubusson and S. G. Dennis *Science* 4, 161 (1977)]. After a 20-min period of acclimation to individual cages, rats are each injected with a predetermined concentration, e.g. 5%, of a formalin solution via the dorsal aspect of one of the rear paws, and the rats are then returned to clear observation cages suspended above mirror panels. During phase 2 of the formalin test, which is defined as the 20-min period of time from 30 to 50 min after formalin injection, nocifensive behaviors in the injected paw of four animals during the session are recorded by observing each animal for one 15-s observation period during each 1-min interval. Nocifensive behaviors include flinching, licking, or biting the injected paw. This process may be repeated with additional subject animals, wherein a number of rats are treated with (+)-bupropion, racemic bupropion or other test or control substances at a predetermined time, for example, 5–10 minutes, prior to formalin injection.

Neuropathic Pain

Nerve injury results in neuroplastic changes that lead to allodynia, a condition characterized by nocifensive behavioral responses to what are normally nonnoxious stimuli conducted by $A\beta$ fibers. In the Chung model of neuropathic pain, allbdynia is produced in the hind limb ipsilateral to the ligation of the L5 and L6 spinal nerves. S. H. Kim and J. M. Chung, *Science* 50, 355 (1992). A within-subjects design in which all animals receive all treatments is used for dose-response studies in the Chung model. Before the start of drug studies, baseline allodynia scores are determined for all animals. Only rats with predetermined threshold scores are considered allodynic and are used in further testing. Drug studies (separate studies for each compound) begin approximately 2 weeks after the nerve ligation surgery. For dose-response experiments, animals are tested over a 2-week period. Test days are separated by 2 to 3 day intervals during which no testing is conducted and no treatment is given. On test days, animals are placed in the individual chambers and allowed to acclimate for 15 to 20 min. After acclimation, baseline scores are determined. Next, animals are treated and then scores are determined 15, 30, 50 and 120 minutes after treatment. This procedure is repeated on test days until each animal has received all treatments for (+)-bupropion, racemic bupropion or other test substances. The treatment order is counterbalanced across all of the animals. For statistical analysis, the time point of peak effect is compared.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference.

Other embodiments are within the following claims.

What is claimed is:

1. A method of treating pain in a human, which comprises administering to a human in need of treatment for said pain, a therapeutically effective amount of (+)-bupropion or a pharmaceutically acceptable salt thereof, substantially free of its (−)-stereoisomer wherein the amount of (+)-bupropion or a pharmaceutically acceptable salt thereof is greater than approximately 90% by weight of the total amount of bupropion.

2. A method of treating pain in a human while avoiding the concomitant liability of adverse effects associated with administration of racemic bupropion, which comprises administering to a human in need of treatment for said pain, a therapeutically effective amount of (+)-bupropion or a pharmaceutically acceptable salt thereof, substantially free of its (−)-stereoisomer, said amount being sufficient to alleviate said pain, but insufficient to cause adverse effects associated with administration of racemic bupropion wherein the amount of (+)-bupropion or a pharmaceutically acceptable salt thereof is greater than approximately 90% by weight of the total amount of bupropion.

3. The method of claim 1 or 2 wherein (+)-bupropion is administered intravenously, by bolus injection, transdermally, intrathecally, or orally.

4. The method of claim 3 wherein (+)-bupropion is administered orally as a tablet or a capsule.

5. The method of claim 1 or 2 wherein the amount administered is from about 10 mg to about 750 mg.

6. The method of claim 5 wherein the amount administered is from about 50 mg to about 600 mg.

7. The method of claim 6 wherein the amount administered is from about 60 mg to about 450 mg.

8. The method of claim 1 or 2 wherein the amount of (+)-bupropion or a pharmaceutically acceptable salt thereof is greater than approximately 90% by weight of the total amount of bupropion.

9. The method of claim 1 or 2 wherein the amount of (+)-bupropion or a pharmaceutically acceptable salt thereof is 99% or more by weight of the total amount of bupropion.

10. The method of claim 1 or 2 wherein the amount of (+)-bupropion or a pharmaceutically acceptable salt thereof, substantially free of its (−)-stereoisomer is administered together with a pharmaceutically acceptable carrier.

11. The method according to claims 1 or 2 wherein (+)-bupropion is administered as the hydrochloride salt.

12. The method of claim 1 or 2 wherein (+)-bupropion is administered in a sustained or controlled release formulation.

13. The method according to claim 1 or 2, wherein said administration is made one to four times per day.

14. The method according to claims 1 or 2, wherein said administration is made daily for 7 days.

15. The method of claim 1 or 2 wherein said pain is chronic pain, neuropathic pain, pain associated with depression, persistent headache or reflex sympathetic dystrophy.

16. A method for treating nicotine addiction in a human, which comprises administering to said human suffering from nicotine addiction, a therapeutically effective amount of (+)-bupropion or a pharmaceutically acceptable salt thereof, substantially free of its (−)-stereoisomer wherein the amount of (+)-bupropion or a pharmaceutically acceptable salt thereof is greater than approximately 90% by weight of the total amount of bupropion.

17. A method of treating nicotine addiction in a human while avoiding the concomitant liability of adverse effects associated with the administration of racemic bupropion, which comprises administering to said human suffering from nicotine addiction, a therapeutically effective amount of (+)-bupropion or a pharmaceutically acceptable salt thereof, substantially free of its (−)-stereoisomer, said amount being sufficient to alleviate nicotine addiction, but insufficient to cause adverse effects associated with administration of racemic bupropion wherein the amount of (+)-bupropion or a pharmaceutically acceptable salt thereof is greater than approximately 90% by weight of the total amount of bupropion.

18. The method of claim 16 or 17 wherein (+)-bupropion is administered intravenously, transdermally, or orally.

19. The method of claim 18 wherein (+)-bupropion is administered orally as a table or a capsule.

20. The method of claim 18 wherein the amount administered is from about 10 mg to about 750 mg.

21. The method of claim 19 wherein the amount administered is from about 50 mg to about 600 mg.

22. The method of claim 20 wherein the amount administered is from about 60 mg to about 450 mg.

23. The method of claim 16 or 17 wherein the amount of (+)-bupropion or a pharmaceutically acceptable salt thereof is 99% or more by weight of the total amount of bupropion.

24. The method of claim 16 or 17 wherein the amount of (+)-bupropion or a pharmaceutically acceptable salt thereof, substantially free of its (−)-stereoisomer, is administered together with a pharmaceutically acceptable carrier.

25. The method according to claims 16 or 17 wherein (+)-bupropion is administered as the hydrochloride salt.

26. The method of claim 16 or 17 wherein (+)-bupropion is administered in a sustained or controlled release formulation.

27. The method of claim 16 or 17 wherein said nicotine addiction is an addiction to smoking, or chewing tobacco.

28. The method of claim 16 or 17 wherein said administration is made one to four times a day.

29. A method for aiding smoking cessation by a human, which comprises administering to said human who smokes a therapeutically effective amount of (+)-bupropion, or a pharmaceutically acceptable salt thereof, substantially free of its (−)-stereoisomer wherein the amount of (+)-bupropion or a pharmaceutically acceptable salt thereof is greater than approximately 90% by weight of the total amount of bupropion.

30. A method for aiding smoking cessation by a human while avoiding the concomitant liability of adverse effects associated with the administration of racemic bupropion, which comprises administering to said human who smokes a therapeutically effective amount of (+)-bupropion, or a pharmaceutically acceptable salt thereof, substantially free of its (−)-stereoisomer, said amount being sufficient to achieve smoking cessation or a reduction in smoking, but insufficient to cause adverse effects associated with the administration of racemic bupropion wherein the amount of (+)-bupropion or a pharmaeutically acceptable salt thereof is greater than approximately 90% by weight of the total amount of bupropion.

31. The method of claim 29 or 30 wherein (+)-bupropion is administered intravenously, by bolus injection, transdermally, intrathecally, or orally.

32. The method of claim 31 wherein (+)-bupropion is administered orally as a tablet or a capsule.

33. The method of claim 29 or 30 wherein the amount administered is from about 10 mg to about 750 mg.

34. The method of claim 33 wherein the amount administered is from about 50 mg to about 600 mg.

35. The method of claim 34 wherein the amount administered is from about 60 mg to about 450 mg.

36. The method of claim 29 or 30 wherein the amount of (+)-bupropion or a pharmaceutically acceptable salt thereof is 99% or more by weight of the total amount of bupropion.

37. The method of claim 29 or 30 wherein the amount of (+)-bupropion or a pharmaceutically acceptable salt thereof, substantially free of its (−)-stereoisomer is administered together with a pharmaceutically acceptable carrier.

38. The method according to claims 29 or 30 wherein (+)-bupropion is administered as the hydrochloride salt.

39. The method of claim 29 or 30 wherein (+)-bupropion is administered in a sustained or controlled release formulation.

40. The method according to claim 29 or 30, wherein said administration is made one to four times per day.

41. A method for treating weight gain associated with smoking cessation by a human, which comprises administering to said human suffering from said weight gain associated with smoking cessation, a therapeutically effective amount of (+)-bupropion, or a pharmaceutically acceptable salt thereof, substantially free of its (−)-stereoisomer wherein the amount of (+)-bupropion or a pharmaceutically acceptable salt thereof is greater than approximately 90% by weight of the total amount of bupropion.

42. A method for treating weight gain associated with smoking cessation by a human while avoiding the concomitant liability of adverse effects associated with the administration of racemic bupropion, which comprises administering to said human suffering from said weight gain associated with smoking cessation, a therapeutically effective amount of (+)-bupropion or a pharmaceutically acceptable salt thereof, substantially free of its (−)-stereoisomer, said amount being sufficient to achieve weight loss, but insufficient to cause the adverse effects associated with administration of racemic bupropion wherein the amount of (+)-bupropion or a pharmaceutically acceptable salt thereof is greater than approximately 90% by weight of the total amount of bupropion.

43. The method of claim 41 or 42 wherein (+)-bupropion is administered intravenously, by bolus injection, transdermally, intrathecally, or orally.

44. The method of claim 43 wherein (+)-bupropion is administered orally as a tablet or a capsule.

45. The method of claim 41 or 42 wherein the amount administered is from about 10 mg to about 750 mg.

46. The method of claim 45 wherein the amount administered is from about 50 mg to about 600 mg.

47. The method of claim 46 wherein the amount administered is from about 60 mg to about 450 mg.

48. The method of claim 41 or 42 wherein the amount of (+)-bupropion or a pharmaceutically acceptable salt thereof is 99% or more by weight of the total amount of bupropion.

49. The method of claim 41 or 42 wherein the amount of (+)-bupropion or a pharmaceutically acceptable salt thereof, substantially free of its (−)-stereoisomer is administered together with a pharmaceutically acceptable carrier.

50. The method according to claims 41 or 42 wherein (+)-bupropion is administered as the hydrochloride salt.

51. The method of claim 41 or 42 wherein (+)-bupropion is administered in a sustained or controlled release formulation.

52. The method according to claim 41 or 42, wherein said administration is made one to four times per day.

53. A pharmaceutical composition which comprises a therapeutically amount of (+)-bupropion or a pharmaceutically acceptable salt thereof, substantially free of its (−)-stereoisomer, and a pharmaceutically acceptable carrier wherein the amount of (+)-bupropion or a pharmaceutically acceptable salt thereof is greater than approximately 90% by weight of the total amount of bupropion.

54. The composition according to claim 53 wherein the amount is about 10 mg to about 750 mg.

55. The composition according to claim 53 which comprises (+)-bupropion hydrochloride and a pharmaceutically acceptable carrier.

56. The composition according to claim 55 wherein said composition is adapted for oral administration.

57. The composition according to claim 55 adapted for intravenous delivery.

58. The composition according to claim 55 for use in a transdermal formulation.

59. The composition according to claim 55 for use as a transdermal patch.

60. The composition of claim 55 wherein said composition is a solid preparation.

61. A sustained release formulation which comprises (+)-bupropion or a pharmaceutically acceptable salt thereof substantially free of its (−)-stereoisomer, and a pharmaceutically acceptable carrier wherein the amount of (+)-bupropion or a pharmaceutically acceptable salt thereof is greater than approximately 90% by weight of the total amount of bupropion.

62. The sustained release formulation of claim 61 wherein said formulation is a tablet, capsule or gelcap.

* * * * *